United States Patent
Bergeron et al.

(10) Patent No.: US 6,817,988 B2
(45) Date of Patent: Nov. 16, 2004

(54) INJECTION DEVICE

(75) Inventors: Luc Bergeron, Boussens (CH); Elena Brioschi, Geneva (CH); Rémy Jacquet, Locle (CH); Jérôme Moulin, St. Maurice (CH); Laurent Soldini, Lausanne (CH)

(73) Assignee: Ares Trading S.A., Vaumarcus (CH)

( * ) Notice: Subject to any disclaimer, the term of this patent is extended or adjusted under 35 U.S.C. 154(b) by 165 days.

(21) Appl. No.: 10/289,911

(22) Filed: Nov. 7, 2002

(65) Prior Publication Data

US 2003/0100861 A1 May 29, 2003

Related U.S. Application Data

(63) Continuation of application No. PCT/IB01/00824, filed on May 14, 2001.

(51) Int. Cl.[7] .............................. A61M 37/00; B67D 5/52
(52) U.S. Cl. ......................... 604/191; 604/119; 222/137
(58) Field of Search ......................... 604/117–119, 121, 604/187, 191, 226, 234, 240; 222/137, 309

(56) References Cited

U.S. PATENT DOCUMENTS 4,109,653 A * 8/1978 Kozam et al. ............... 604/191
4,114,619 A    9/1978 Wagner ....................... 604/117
5,445,614 A * 8/1995 Haber et al. ................. 604/89
5,464,396 A * 11/1995 Barta et al. .................. 604/191
5,665,067 A * 9/1997 Linder et al. ................ 604/82
5,961,494 A * 10/1999 Hogan ........................ 604/191
6,228,065 B1 * 5/2001 Lynn .......................... 604/191

FOREIGN PATENT DOCUMENTS

DE      26 20 358      11/1977
DE      37 30 469      6/1988

* cited by examiner

Primary Examiner—Anhtuan T. Nguyen
(74) Attorney, Agent, or Firm—Sturm & Fix LLP

(57) ABSTRACT

The invention provides an injection device comprising an open cavity, an injection needle projecting from the bottom of this cavity, a first leakproof compartment delimited by a first section of a mobile barrier, first devices for displacing the said first section of a mobile barrier to vary the volume of the compartment, at least one passage communicating between the said first leakproof compartment and the said cavity, a second leakproof compartment for a product to be injected, delimited by a second section of a mobile barrier, and second devices for displacing the said second section of a mobile barrier to vary the volume of the compartment. The said first and second leakproof compartments extend longitudinally within a tubular body. The cavity is located at one end of this tubular body, while the said first and second devices for displacing the said first and second sections of a mobile barrier are accessible at the other end of the said tubular body.

26 Claims, 3 Drawing Sheets

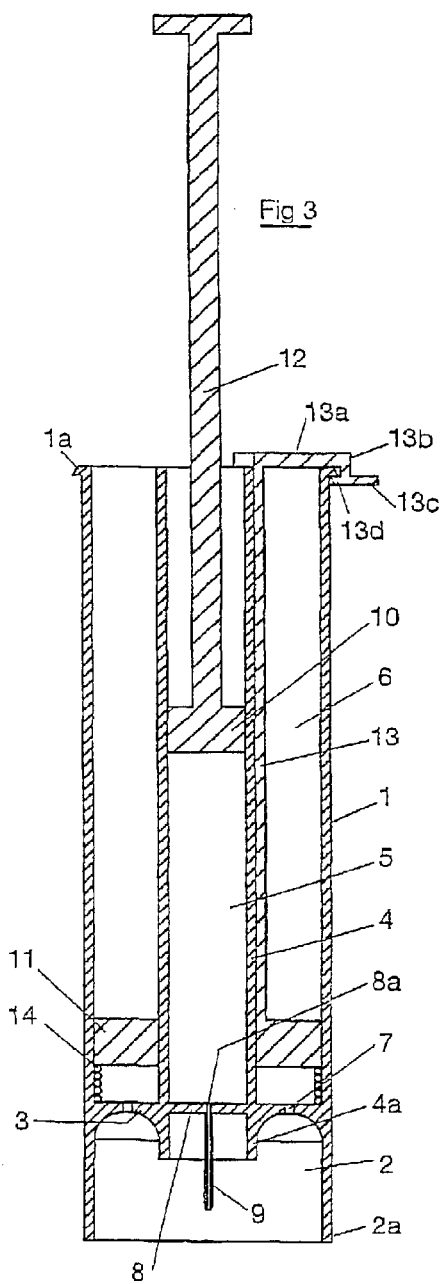
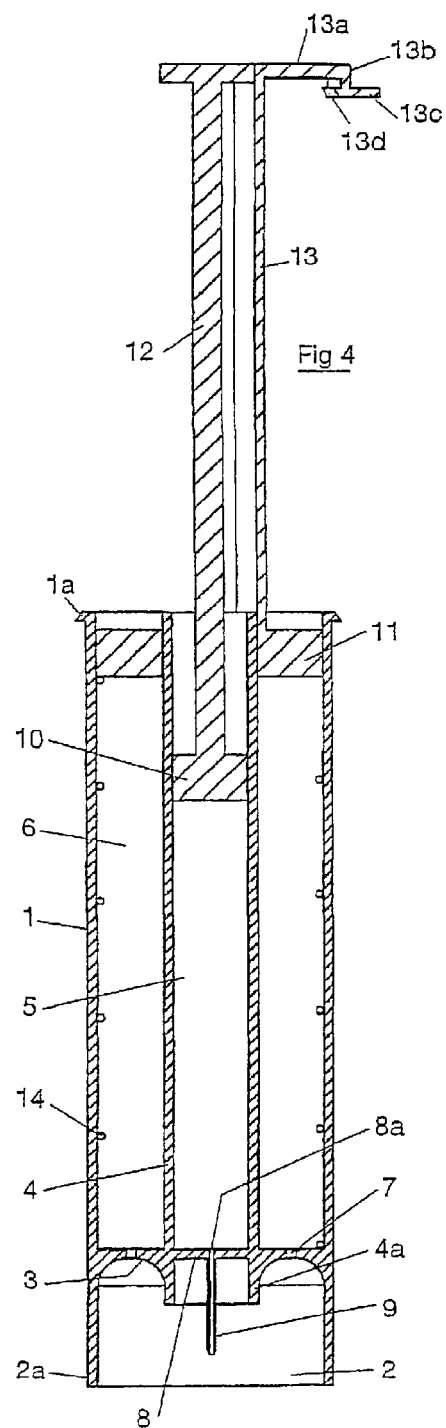

INJECTION DEVICE

CROSS REFERENCE TO RELATED APPLICATIONS

This application is a Continuation application of PCT/IB01/00824 filed May 14, 2001, claiming priority of European Application No. 00810414.3 filed may 15, 200, entitled Injection Device, which are included in their entirety by reference made hereto.

FIELD OF THE INVENTION

The invention relates to an injection device.

BACKGROUND OF THE INVENTION

An injection device using suction has been proposed in U.S. Pat. No. 4,114,619. The proposed device has an open cavity with an injection needle projecting from the bottom of the cavity. The open cavity is applied to the skin. When the opening of the cavity is placed correctly sensors activate a suction piston which creates a vacuum in the cavity. This vacuum draws the skin towards the bottom of the cavity and then causes penetration by the injection needle projecting from the bottom of the cavity. A second detector, consisting of a pressure transducer, activates the piston of the injection syringe.

The purpose of the device of U.S. Pat. No. 4,114,619 is to achieve complete automation of the injection process once the opening of the cavity is correctly placed in contact with this tissue. In consequence the design of the device for executing this automatic process is relatively complex.

SUMMARY OF THE INVENTION

It is an object of the present invention to provide an injection device of simplified design.

It is a further object of the invention to provide an injection device that can be simply manufactured, at low cost.

It is a further object of the invention to provide an injection device that is easily portable.

The invention exploits the concept which consists of making the cutaneous tissue penetrate inside the needle rather than the inverse, as in traditional injection syringes. The invention provides a device of the simplest possible design so that it can be manufactured at low cost and be simple and easy to use. This result is achieved by creating in the injection area, as in the device mentioned above, a vacuum by the use of an open cavity whose opening is applied to the skin so as to draw it up against the injection needle projecting from the bottom of the cavity.

The invention provides an injection device having an open cavity whose opening is delimited by an annular rim intended for application to the skin of a subject under treatment, an injection needle projecting from the bottom of the cavity, its forward end being set back in respect of the annular rim, a first, leakproof compartment delimited by a first mobile barrier, means for displacing the first mobile barrier so as to vary the volume of the first compartment, at least one communicating passage between the first leakproof compartment and the cavity, a second leakproof compartment for a product to be injected, delimited by a second mobile barrier, a second means for displacing the said second section of a mobile barrier so as to vary the volume of the second leakproof compartment, and an opening to enable the second leakproof compartment to communicate with the said injection needle.

DETAILED DESCRIPTION OF THE INVENTION

In the case of self-injection the person performing the injection does not himself have to make the needle penetrate the cutaneous tissue, which is a notable improvement from the psychological standpoint. The drawing up of the skin reduces the perception of pain caused by the penetration of the needle. The depth of needle penetration is perfectly regulated by the length to which the needle projects from the bottom of the cavity, a safety feature likely to be reassuring, particularly to the person who must perform self-injection.

The attached drawings illustrate, schematically and by way of example, one embodiment of the injection device to which the invention refers.

FIG. 3 is a view similar to FIG. 1 showing the device in a second position;

FIG. 4 is a view similar to FIG. 1 showing the device in a third position;

Figure 2:
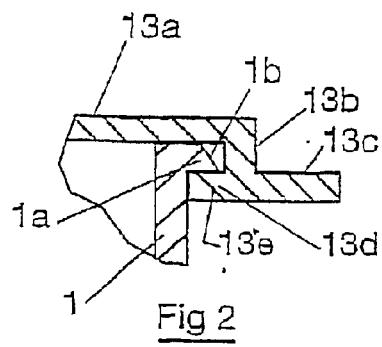
FIG. 2 is an enlarged view of a detail of FIG. 1.

The device illustrated has a tubular cylindrical body 1 having at one end an open cavity 2 the bottom of which is delimited by an annular wall 3 extending around a cylindrical wall 4 centred on the longitudinal axis of the tubular body 1. This cylindrical wall 4 extends from the open end of the tubular body 1, opposite to the open cavity 2, into the interior of the latter, in the bottom of which a portion 4a of this cylindrical wall 4 projects.

The cylindrical wall 4 divides the interior space of the tubular body 1 adjoining the annular wall 3 opposite the open cavity 2 into two elongated compartments, of which one, 5, has an annular section forming a cylinder concentric with the axis of the tubular body 1, the other, 6, having an annular section concentric with the cylindrical compartment 5 which it surrounds.

Openings 7 are made through the wall 3 to place the compartment 6 in communication with the open cavity 2. The cylindrical compartment 5 is closed at the level of the wall 3 by a barrier 8 which forms one piece with an injection needle 9 extending inside the open cavity 2, its forward end being set back from the rim 2a bounding the opening of the cavity 2. If the barrier 8 is not directly formed by a single piece moulded together with the tubular body 1 it can be soldered or glued on. Its centre has a perforation 8a to place the channel of the injection needle in communication with the cylindrical compartment 5.

Each of the compartments 5, 6 encloses a piston, 10, 11 respectively. The piston 10 forms one piece with a plunger 12, while the piston 11 forms one piece with a plunger 13 which in section takes the form of an annular sector with its concave surface fitting tightly against the exterior surface of the cylindrical wall 4. The end of the plunger 13 located outside the tubular body 1 forms one piece with a circular sector 13a the exterior extremity of which terminates in a lip 13b which in turn forms one piece with a lug 13c (FIG. 2).

A locking element 13d is located within the lip 13b and terminates in a bevel 13e. The end of the wall of the tubular body 1 consists of an annular lip 1a delimited externally by a bevel 1b. As is shown in FIG. 2 the two bevels 1b and 13e are designed as detents, that is to say, they are designed to ensure, when locked together, that the plunger 13 and the piston 11 stay in position along the axis of the tubular body 1 when subjected to an axial force which tends to push the plunger 13 out of the tubular body 1. On the other hand, the bevels 1b and 13e allow the lip 13d to be locked onto the lip 1a of the tubular body 1 when the plunger 13 and the piston 11 are displaced along their axis from the open end of the compartment 6 towards its closed end, creating a component of centripetal force which can displace the lip 13b when the bevel 13e pushes against the bevel of the lip 1a to allow the lip 13d to pass the lip 1a of the tubular body 1, until the lip 13b locks under the lip 1a. This, of course, presupposes adequate elasticity in the circular sector 13a. For this purpose it is advantageous to use a material which can be deformed elastically.

Figure 1:
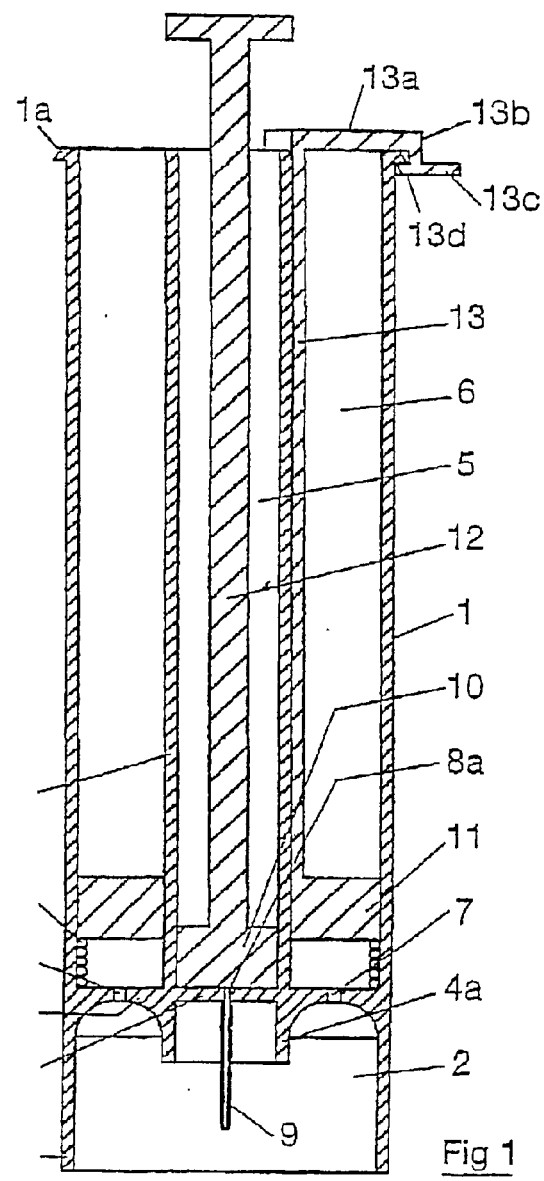
FIG. 1 is a section along the axis of this embodiment showing the device in a first position.

A helicoidal spring 14 is placed in the compartment 6 between the bottom of the compartment delimited by the annular wall 3 and the piston 11. When the piston 11 compresses the spring 14 against the bottom 3 of the compartment 6 the circular sector 13a forming one piece with the plunger 13 of the piston 11 is locked to the lip 1a of the tubular body 1a [sic] as explained above. When not in use the various elements of the device described are in the position illustrated in FIG. 1.

To perform an injection using this device the required amount of the product to be injected is drawn in, as in the case of a traditional syringe, by placing the forward end of the injection needle 9 in the appropriate product and drawing in the desired dose of the product by displacing the piston 10 by means of the plunger 12, as is shown in FIG. 3.

The opening 2a of the cavity 2 is then applied to the surface of the skin (not shown) through which the injection is to be made. The piston 11 is freed by unlocking the lip 13d of the circular sector 13a from the lip 1a of the tubular body 1 by deforming the lug 13c upwards. The freed piston 11 allows the pressure developed by the release of the spring 14 to push it towards the open end of the compartment 6. Since the cavity 2 is closed by the skin to which its rim 2a is applied the displacing of the piston 11 creates a vacuum within the compartment 6 and the cavity 2 which communicates with it via the openings 7. This vacuum has the effect of deforming the portion of skin which is inside the rim 2a of the cavity 2 in the direction of the bottom of the cavity 2, thus forcing the end of the needle through the skin resting against the rim of the portion 4a of the cylindrical wall 4 projecting from the bottom of the cavity 2 concentrically with the injection needle 9. The various elements of the device are then in the position illustrated in FIG. 4, ready for the injection proper.

Figure 5:
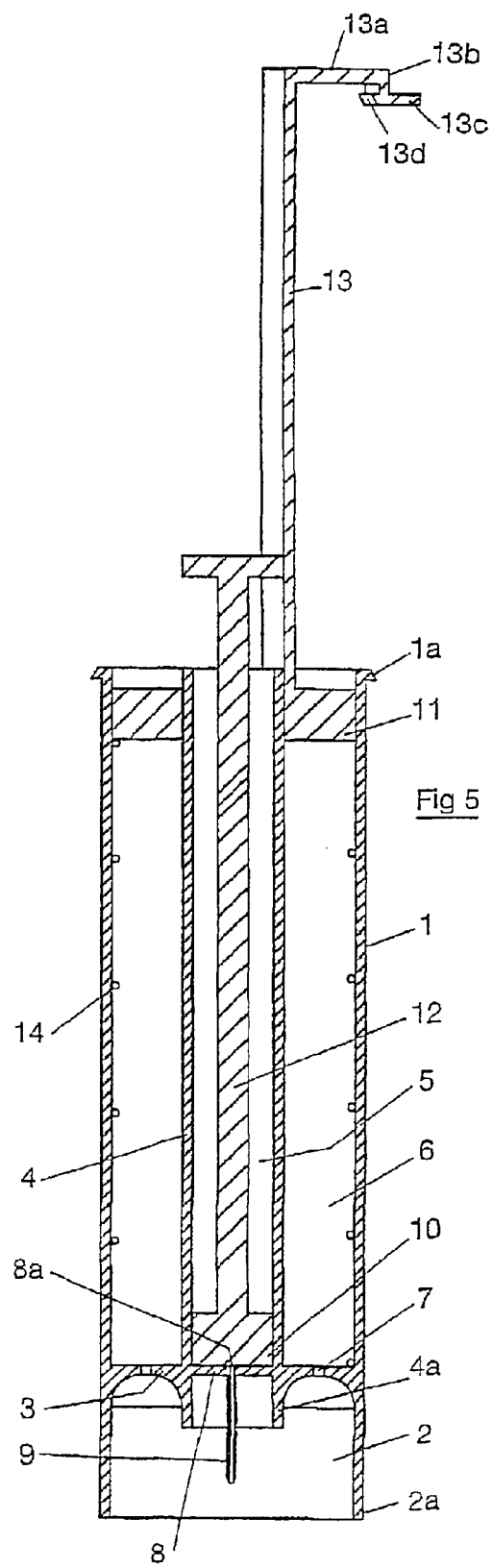
FIG. 5 is a view similar to FIG. 1 showing the device in a fourth position.

For this purpose the plunger 12 is then pushed back within the compartment 5 until it rests against the barrier 8 delimiting the bottom of the compartment 5, as shown in FIG. 5. The device is withdrawn simply by pushing back the plunger 13 forming one piece with the piston 11, thus once more raising the pressure and then making it possible to separate the opening 2a of the cavity 2 from the skin which is no longer drawn in by the vacuum in the cavity 2. The locking element 13d is then once again locked under the lip 1a of the cylindrical body 1 to hold the piston 11 in the position of FIG. 1 against the pressure exerted upon it by the spring 14 which is once more compressed at the bottom of the annular compartment 6.

The device of the invention may be made of plastic, metal or glass. It is preferred that the pistons and cylindrical body be made of plastic.

In a preferred embodiment, the device is designed for a single use.

In a further preferred embodiment, the needle length can be varied, thus allowing control of the depth of penetration.

What is claimed is:

1. A handheld injection device comprising:

an open cavity having a rim, the rim being capable of forming an airtight seal when applied to the skin of a patient;

a first piston in communication with the open cavity, for creating suction therein;

a needle projecting into the open cavity, but not projecting beyond the rim;

a second piston for containing a product to be injected, the second piston being in communication with the needle;

wherein withdrawal of the first piston creates suction in the open cavity, causing the patient's skin to be sucked into the cavity and to be pierced by the needle, and actuation of the second piston causes the product to be injected;

wherein the first and second pistons are located within a cylindrical body, the cylindrical body having the needle at one end and actuating means for the pistons at another end.

2. A device according to claim 1, wherein said cylindrical body comprises a first central cylinder surrounded by a second annular cylinder in which are located respectively said first and second pistons.

3. An injection device comprising:

an open cavity, the opening of which is delimited by an annular rim intended to be applied to the skin of a subject under treatment, an injection needle projecting from the bottom of the cavity, its forward end being set back in relation to the said annular rim;

a first leakproof compartment delimited by a first section of a mobile barrier;

first means for displacing the said first section of a mobile barrier in order to vary the volume of said first compartment;

at least one passage communicating between the first leakproof compartment and the said cavity, a second leakproof compartment for a product to be injected, delimited by a second section of a mobile barrier;

second means for displacing the said second section of a mobile barrier in order to vary the volume of the second leakproof compartment and an opening communicating between the second leakproof compartment and the said injection needle, characterized in that the said first and second leakproof compartments extend longitudinally within a tubular body, that the said cavity is located at one end of the tubular body, while the said first and second means for displacing the said first and second sections of a mobile barrier respectively of the said first and second leakproof compartments are accessible at the other end of the said tubular body.

4. A device according to claim 3, wherein the said first leakproof compartment has an annular section surrounding the said second leakproof compartment.

5. A device according to claim 4, wherein it includes elastic pressure devices acting on the said first section of a mobile barrier to increase the volume of the said first compartment and locking elements to hold the said first section of a mobile barrier in a position in which the said elastic devices are compressed, equivalent to the minimum volume of the said first compartment.

6. A device according to claim 5, wherein the said locking elements form one piece with both the said first devices for displacing the said first section of a mobile barrier and with the said tubular body.

7. A device according to claim 6, wherein each of the said first and second sections of a mobile barrier is formed by a piston sliding within its respective compartment.

8. A device according to claim 7, wherein an annular wall extends concentrically around the portion of the said injection needle which projects at the bottom of the said cavity, at approximately half the distance between the bottom and the forward end of the said injection needle.

9. A device according to claim 6, wherein an annular wall extends concentrically around the portion of the said injection needle which projects at the bottom of the said cavity, at approximately half the distance between the bottom and the forward end of the said injection needle.

10. A device according to claim 5, wherein each of the said first and second sections of a mobile barrier is formed by a piston sliding within its respective compartment.

11. A device according to claim 10, wherein an annular wall extends concentrically around the portion of the said injection needle which projects at the bottom of the said cavity, at approximately half the distance between the bottom and the forward end of the said injection needle.

12. A device according to claim 5, wherein an annular wall extends concentrically around the portion of the said injection needle which projects at the bottom of the said cavity, at approximately half the distance between the bottom and the forward end of the said injection needle.

13. A device according to claim 4, wherein each of the said first and second sections of a mobile barrier is formed by a piston sliding within its respective compartment.

14. A device according to claim 13, wherein an annular wall extends concentrically around the portion of the said injection needle which projects at the bottom of the said cavity, at approximately half the distance between the bottom and the forward end of the said injection needle.

15. A device according to claim 4, wherein an annular wall extends concentrically around the portion of the said injection needle which projects at the bottom of the said cavity, at approximately half the distance between the bottom and the forward end of the said injection needle.

16. A device according to claim 3, wherein it includes elastic pressure devices acting on the said first section of a mobile barrier to increase the volume of the said first compartment and locking elements to hold the said first section of a mobile barrier in a position in which the said elastic devices are compressed, equivalent to the minimum volume of the said first compartment.

17. A device according to claim 16, wherein the said locking elements form one piece with both the said first devices for displacing the said first section of a mobile barrier and with the said tubular body.

18. A device according to claim 17, wherein each of the said first and second sections of a mobile barrier is formed by a piston sliding within its respective compartment.

19. A device according to claim 18, wherein an annular wall extends concentrically around the portion of the said injection needle which projects at the bottom of the said cavity, at approximately half the distance between the bottom and the forward end of the said injection needle.

20. A device according to claim 17, wherein an annular wall extends concentrically around the portion of the said injection needle which projects at the bottom of the said cavity, at approximately half the distance between the bottom and the forward end of the said injection needle.

21. A device according to claim 16, wherein each of the said first and second sections of a mobile barrier is formed by a piston sliding within its respective compartment.

22. A device according to claim 21, wherein an annular wall extends concentrically around the portion of the said injection needle which projects at the bottom of the said cavity, at approximately half the distance between the bottom and the forward end of the said injection needle.

23. A device according to claim 16, wherein an annular wall extends concentrically around the portion of the said injection needle which projects at the bottom of the said cavity, at approximately half the distance between the bottom and the forward end of the said injection needle.

24. A device according to claim 3, wherein each of the said first and second sections of a mobile barrier is formed by a piston sliding within its respective compartment.

25. A device according to claim 24, wherein an annular wall extends concentrically around the portion of the said injection needle which projects at the bottom of the said cavity, at approximately half the distance between the bottom and the forward end of the said injection needle.

26. A device according to claim 3, wherein an annular wall extends concentrically around the portion of the said injection needle which projects at the bottom of the said cavity, at approximately half the distance between the bottom and the forward end of the said injection needle.

* * * * *